(12) United States Patent
Hwang et al.

(10) Patent No.: US 8,435,957 B2
(45) Date of Patent: May 7, 2013

(54) USE OF LIGNAN COMPOUND FOR ANTI-WRINKLE TREATMENT

(75) Inventors: Jae-Kwan Hwang, Kyeonggi-Do (KR); Hae Ji Lee, Incheon (KR); Jae Young Lee, Seoul (KR); Jae-Seok Shim, Kyeonggi-Do (KR); Jeong Hwan Kim, Seoul (KR); Do Un Kim, Gyeonggi-Do (KR); Heechul Chung, Gyeonggi-Do (KR); Jae Youn Chung, Gyeonggi-Do (KR)

(73) Assignees: Biocare Co., Ltd., Seoul (KR); Newtree Co., Ltd., Sungnam, Gyeonggi-Do (KR)

( * ) Notice: Subject to any disclaimer, the term of this patent is extended or adjusted under 35 U.S.C. 154(b) by 219 days.

(21) Appl. No.: 12/665,206

(22) PCT Filed: Jun. 20, 2008

(86) PCT No.: PCT/KR2008/003547
§ 371 (c)(1),
(2), (4) Date: Dec. 23, 2010

(87) PCT Pub. No.: WO2008/156345
PCT Pub. Date: Dec. 24, 2008

(65) Prior Publication Data
US 2012/0288579 A1   Nov. 15, 2012

(30) Foreign Application Priority Data
Jun. 20, 2007   (KR) .................. 10-2007-0060178

(51) Int. Cl.
*A61K 31/70*   (2006.01)

(52) U.S. Cl.
USPC .............................. 514/22; 424/401; 424/776

(58) Field of Classification Search ................ None
See application file for complete search history.

(56) References Cited

U.S. PATENT DOCUMENTS
4,670,264 A * 6/1987 Warren et al. ................. 424/769

OTHER PUBLICATIONS

"Cosmetic compositions containing lignans as adlpogenesis enhancers" Research Disclosure Database No. 530010, published in Jun. 2008 (Electronic Publication Date: May 8, 2008).

* cited by examiner

*Primary Examiner* — Susan Hoffman
(74) *Attorney, Agent, or Firm* — Edwards Wildman Palmer LLP

(57) ABSTRACT

The present invention relates to a novel use of lignan compounds, which are isolated and purified from nutmeg or the aril of nutmeg for anti-wrinkle, and more particularly, the present invention relates to a novel use for anti-wrinkle of an extract of the nutmeg or an extract of the aril of the nutmeg, fragrin A, austobailignan 7, licarin E, and macelignan. The extracts and lignan compounds of the present invention have activities in suppressing collagen degradation enzyme-1 (MMP-I, matrix metalloprotei-nase-1) and formation of new collagen (type-1 procollagen), thereby having effect on inhibitng wrinkle caused by photoaging. Accordingly, the extracts and lignan compounds of the present invention may be useful for preventing or treating wrinkle caused by photoaging.

3 Claims, 7 Drawing Sheets

A B C D

A B C D

USE OF LIGNAN COMPOUND FOR ANTI-WRINKLE TREATMENT

CROSS-REFERENCES TO RELATED APPLICATIONS

This application is a U.S. national phase application, pursuant to 35 U.S.C. §371 of PCT/KR2008/003547, filed Jun. 20, 2008, designating the United States, which claims priority to Korean Application No. 10-2007-0060178, filed Jun. 20, 2007. The entire contents of the aforementioned patent applications are incorporated herein by this reference.

TECHNICAL FIELD

This application claims the priority of Korean Patent Application No. 10-2007-0060178, filed on 20 June, 2007, the disclosure of which is incorporated herein by reference.

The present invention relates to a novel use of lignan compounds, which are isolated and purified from nutmeg or the aril of nutmeg for reducing wrinkle, and more particularly, the present invention relates to a novel anti-wrinkle composition comprising fragrin A represented by Formula 1, austobailignan 7 represented by Formula 2, licarin E represented by Formula 3, and macelignan represented by Formula 4 as effective component, the uses of the said extracts or compounds for reducing wrinkle, inducing collagen synthesis, and suppressing collagen decomposition, and the methods for inhibiting wrinkle, inducing collagen synthesis, and suppressing collagen decomposition by using the said extracts or compounds.

BACKGROUND ART

In general, wrinkles is a part of natural aging, which is caused by repeated muscular contractions for a long period of time. Skin aging is broadly classified into intrinsic aging, or natural aging and extrinsic aging. The natural aging is difficult to be regulated, because it is caused by genetic factors, but extrinsic aging is easy to be regulated artificially, because it is caused by environmental factors. Thus, studies on the prevention of extrinsic aging have been continued, and particularly, studies on the prevention of wrinkle formation resulting from extrinsic photoaging, which progresses due to long-term exposure to UV radiation, have received attention (Gilchre st B. A., J. Am. Acad. Dermatol., 1989:21:610-613).

The clinical characteristics of photoaging, that is, extrinsic skin aging, are that the skin becomes rough and loses elasticity, irregular pigmentation occurs and deep wrinkles increase. Particularly, it has been found that photoaging has a great effect on the formation of wrinkles on the face and head, which are important objects of beauty, and thus, as fundamental studies on the development of anti-wrinkle cosmetic products, studies on photoaging and wrinkle formation in human skin or animal models have been actively conducted. With respect to photoaging and wrinkle formation, the results of studies on changes in basic physiological metabolisms, such as collagen synthesis and degradation, have been reported to date (Lavker R. M., Blackwell science Inc., 1995:123-135).

External factors influencing skin aging include wind, temperature, humidity, cigarette smoke, environmental pollution and UV radiation, and particularly, aging caused by UV radiation is called "photoaging". When the skin is exposed to a large amount of UV radiation, a high concentration of reactive oxygen species are produced in the skin to damage the enzymatic and non-enzymatic antioxidant defense systems of the skin. For this reason, collagen, that is, the main protein of skin tissue, is remarkably reduced, and matrix metalloproteinase-1 (MMP-1) has an important effect on the reduction of collagen. Matrix metalloproteinase-1 (MMP-1) is an enzyme involved in the degradation of the extracellular matrix and the basement membrane, and it has been reported that the activity of matrix metalloproteinase-1 in the skin is increased due to UV radiation to remarkably degrade collagen, and thus matrix metalloproteinase-1 has an important effect on collagen degradation and plays a very important role in wrinkle formation (Sim G. S., Kim J. H et al., Kor. J. Biotechnol. Bioeng., 2005:20(1):40-45).

Some of active ingredients for anti-wrinkle, which have been developed to date, have problems in that they cannot be used as cosmetic materials, are very unstable and are not easy to deliver to the skin, such that a special stabilizing system and delivery system are required, and the effect thereof on the reduction of skin wrinkles is not visible. For this reason, interest in skin-protecting agents containing retinoid has recently been increased. Currently, retinoid is used as a means for solving photoaging phenomena, such as wrinkles resulting from sunlight, skin thickening, skin drooping and a decrease in skin elasticity. However, retinoid has a problem in that it is a very unstable compound, which is sensitive to UV light, moisture, heat and oxygen such that a chemical change therein easily occurs. In attempts to solve this problem, studies focused on developing effective components derived from natural resources have been conducted.

DISCLOSURE

Technical Problem

Accordingly, the present inventors have conducted long-term studies to find a natural compound, which can be effectively used to reduce wrinkles, and as a result, have found that an extract of nutmeg or the aril of nutmeg and as lignan compounds, fragrin A, austobailignan 7, licarin E, and macelignan which are isolated and purified from an extract of nutmeg or the aril of nutmeg have excellent effect on reducing wrinkle, thereby completing the present invention.

Accordingly, it is an object of the present invention to provide a novel use of an extract of nutmeg or the aril of nutmeg and as lignan compounds, fragrin A, austobailignan 7, licarin E, and macelignan which are isolated and purified from an extract of nutmeg or the aril of nutmeg.

Technical Solution

To achieve the above objects, the present invention provides an anti-wrinkle composition comprising one lignan compound selected from the group consisting of fragrin A represented by Formula 1, austobailignan 7 represented by Formula 2, licarin E represented by Formula 3, and macelignan represented by Formula 4 as effective component.

In addition, the present invention provides a use of the said lignan compounds for preparing agent for reducing wrinkle, inducing collagen synthesis, and suppressing collagen degradation.

In addition, the present invention provides a method comprising administrating or applying an effective amount of the said lignan compounds to a subject in need thereof for reducing wrinkle, inducing collagen synthesis, and suppressing collagen degradation.

In addition, the present invention provides an anti-wrinkle composition comprising an extract of nutmeg or the aril of nutmeg as an effective component.

In addition, the present invention provides a use of an extract of nutmeg or the aril of nutmeg for preparing an agent for reducing wrinkle, inducing collagen synthesis, and suppressing collagen degradation.

In addition, the present invention provides a method comprising administrating or applying an effective amount of an extract of nutmeg or the aril of nutmeg to a subject in need thereof for reducing wrinkle, inducing collagen synthesis, and suppressing collagen degradation.

Hereafter, the present invention will be described in detail.

The present invention is characterized by providing novel use of an extract of nutmeg or the aril of nutmeg and as lignan compounds, fragrin A represented by Formula 1, austobailignan 7 represented by Formula 2, licarin E represented by Formula 3, and macelignan represented by Formula 4 which are isolated and purified from an extract of nutmeg or the aril of nutmeg.

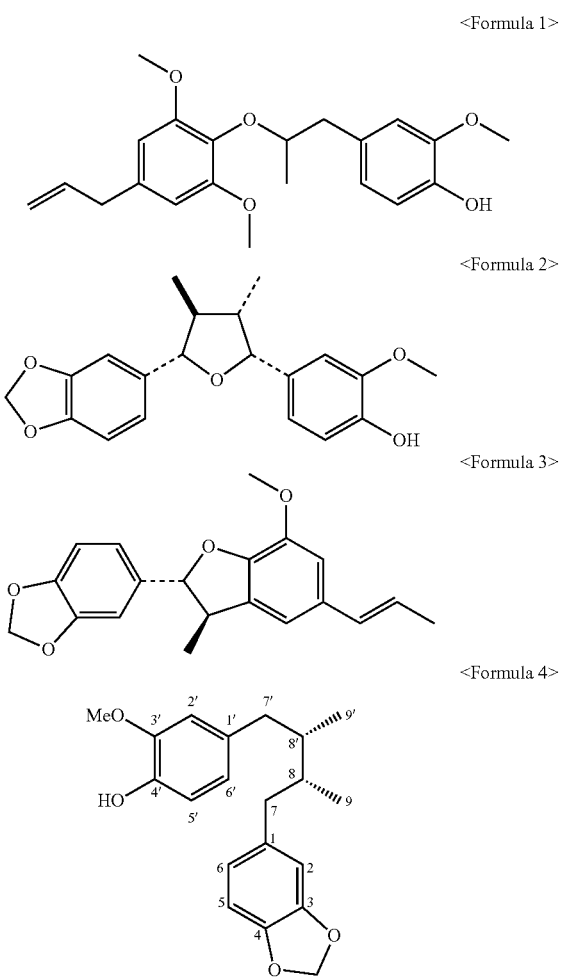

<Formula 1>

<Formula 2>

<Formula 3>

<Formula 4>

Meanwhile, the nutmeg is a nut of *Myristica fragrans* which is a perennial plant cultured in tropical regions, and has been used as spices for a long time. In addition, the aril of nutmeg is peel region of the said fruit of *Myristica fragrans* and is reported that it has inhibition of proliferation of *Helicobacter pylori*(In Vivo., 17; 541-4, 2003), activation of detoxification in liver (*Food Chem. Toxicol.*, 31; 517-21, 1993), chemical prevention of skin verruca (*Cancer Lett.*, 56; 59-63, 1991), anti-inflammation activity (*Jpn. J. Pharmacol.*, 49; 155-63, 1999). However, the relationship between the nutmeg or the aril of nutmeg and effect on reducing wrinkle thereof have never been reported as yet.

The lignan compounds of the present invention can be isolated and purified using a conventional extraction and chromatography method from nutmeg or the aril of nutmeg.

Extraction from nutmeg or the aril of nutmeg is performed with, for example, water, organic solvents such as C1-C6 organic solvent such as ethanol, methanol, propanol, isopropanol, and butanol, acetone, ether, chloroform, ethyl acetate, methylene chloride, hexane, cyclohexane, petroleum ether, diethylether, and benzene and the like, used alone or in a mixture. Preferably, it is extracted by using water or C1-C6 organic solvent.

Although the ratio of a solvent to nutmeg or the aril of nutmeg in the extraction process is not specifically limited, a solvent may be added to nutmeg or the aril of nutmeg powder in an amount 1-20 times the weight of the powder. Preferably, a solvent may be added to the powder in an amount 2-5 times the weight of the powder in order to increase extraction efficiency.

The extraction process is preferably carried out at room temperature under atmospheric pressure, and the extraction is 6-96 hours, and preferably 36-72 hours, even though it varies depending on the extraction time. Also, in the extraction process, a shaker may be used to further increase extraction efficiency.

Before use in the extraction process, nutmeg or the aril of nutmeg may be washed after being harvested or dried after being washed. The drying process may be carried out using any one of sun-drying, shade-drying, hot-air drying and natural drying. Also, to increase extraction efficiency, nutmeg or the aril of nutmeg may be used after it is ground with a grinder.

Preparation of extract of nutmeg or the aril of nutmeg is performed by, for example, pouring dried nutmeg or the aril of nutmeg into extraction device with 4 to 10 times the weight of extraction solvent, leaving it for 1-5 days, extracting, concentrating by concentration device and drying, and finally the extract is produced.

The extract obtained as described above is subjected to silica gel column chromatography to obtain fractions according to polarity, and the separated specific fraction is subjected to reverse phase column chromatography and high-performance liquid chromatography (HPLC), thus separating fragrin A, austobailignan 7, licarin E, and macelignan from the fraction. All of the said fragrin A, austobailignan 7, licarin E, and macelignan are isolated and purified from nutmeg and the aril of nutmeg. However, the method for extracting and separating the active ingredients is not necessarily limited to the above-described method.

The above-described inventive extract of nutmeg, the aril of nutmeg and fragrin A, austobailignan 7, licarin E, and macelignan which is isolated and purified from nutmeg and the aril of nutmeg concentration-dependently inhibit the production of matrix metalloproteinase-1 (MMP-1) in human skin fibroblasts, caused by UV radiation, and increase the synthesis of type-1 procollagen. In addition, when hairless mice radiated with UV light was treated with the inventive composition, the synthesis of collagen in the mice was increased.

Accordingly, the present invention provides an antiwrinkle composition comprising extract of nutmeg, the aril of nutmeg and fragrin A, austobailignan 7, licarin E, and macelignan which is isolated and purified from nutmeg and the aril of nutmeg as an effective component. The said composition may be the composition for cosmetics or food.

The said composition for cosmetics may be prepared by well known skills in the art including one or more conventional excipient and additives as well as an extract of nutmeg, the aril of nutmeg and fragrin A, austobailignan 7, licarin E, and macelignan which is isolated and purified from nutmeg and the aril of nutmeg.

More particularly, a composition for cosmetics of the present invention contains extract of nutmeg, the aril of nutmeg and fragrin A, austobailignan 7, licarin E, and macelignan which is isolated and purified from nutmeg and the aril of nutmeg as an effective component, and may be prepared in the form of basic cosmetics (lotions, cream, essence, cleansers such as cleansing foam and cleansing water, pack, body oil, massage cream), coloring cosmetics (foundation, lip-stick, mascara, make-up base), hair care composition (shampoo, rinse, hair conditioner, hair gel) and soap with dermatologically acceptable excipients. The said excipients may comprise, but not limited thereto, skin softener, skin infiltration enhancer, colorant, odorant, emulsifier, thickener, or solvent. In addition, it is possible to add fragrance, a pigment, bactericidal agent, an antioxidant, a preservative, moisturizer and the like, and to add thickening agents, inorganic salts or synthetic polymers for improving physical properties.

For example, in case of manufacturing a cleanser and soap comprising extract of nutmeg, the aril of nutmeg and fragrin A, austobailignan 7, licarin E, and macelignan which is isolated and purified from nutmeg and the aril of nutmeg, they may be prepared easily by adding an extract of the present invention or lignan compounds to conventional cleanser or soap base. In case of manufacturing a cream, it may be prepared by adding an extract of an extract of the present invention or lignan compounds to conventional oil-in-water cream base. In addition, it is possible to add a fragrance, a chelating agent, a pigment, an antioxidant, a preservative, and the like, and to add proteins, minerals or synthetic polymers for improving physical properties.

An extract of nutmeg, the aril of nutmeg and fragrin A, austobailignan 7, licarin E, and macelignan which is isolated and purified from nutmeg and the aril of nutmeg of the present invention may be properly comprised by the form of composition for cosmetics in the range of 0.005-10 wt %, and preferably 0.01-5 wt %, based on the total weight of a formulation. If the composition is added in an amount of less than 0.005 wt %, it will provide low effect in reducing wrinkle, and if it is added in an amount of more than 10 wt %, it will show no significant difference in reducing wrinkle while increasing only their addition amount.

Further, an extract of nutmeg, the aril of nutmeg and fragrin A, austobailignan 7, licarin E, and macelignan which is isolated and purified from nutmeg and the aril of nutmeg of the present invention may be provided in the form of composition for food. The composition for food of the present invention may comprise all kinds of forms including functional food, nutritional supplement, health food, and food additives.

For example, as a health food, an extract of nutmeg, the aril of nutmeg and fragrin A, austobailignan 7, licarin E, and macelignan which is isolated and purified from nutmeg and the aril of nutmeg of the present invention may be prepared into tea, juice, and drink for drinking or may be prepared into granules, capsules, or powder for uptake. Also, conventional active ingredient which is well known as having activity in reducing and preventing wrinkle may be mixed with an extract of nutmeg, the aril of nutmeg and fragrin A, austobailignan 7, licarin E, and macelignan which is isolated and purified from nutmeg and the aril of nutmeg of the present invention so as to prepare a composition.

Also, for preparing functional foods, beverages (including alcoholic beverages), an extract of nutmeg, the aril of nutmeg and fragrin A, austobailignan 7, licarin E, and macelignan which is isolated and purified from nutmeg and the aril of nutmeg of the present invention may be added to fruits, and their processed foods (e.g. canned fruit, bottled fruit, jam, marmalade etc.), fishes, meats, and their processed foods (e.g. ham, sausage, corn beef etc.), breads and noodles (e.g. Japanese noodle, buckwheat noodle, Chinese noodle, spaghetti, macaroni etc.), fruit juice, drinks, cookies, toffee, dairy products (e.g. butter, cheese etc.), vegetable oil, margarine, vegetable protein, retort food, frozen food, various seasonings (e.g. soybean paste, soybean sauce, sauce etc.) so as to prepare a composition.

In addition, an extract of the present invention or lignan compounds may be prepared in a form of powder or extract for food additives.

An extract of the present invention or lignan compounds of the present invention may be properly combined by the form of composition for food preferably in the range of 0.0001 to 50% based on the total weight of a food.

In addition, the present invention provides a use of an extract of nutmeg, the aril of nutmeg and fragrin A, austobailignan 7, licarin E, and macelignan which is isolated and purified from nutmeg and the aril of nutmeg of the present invention for preparing reagent for reducing wrinkle. Also, it provides a use of an extract of nutmeg, the aril of nutmeg and fragrin A, austobailignan 7, licarin E, and macelignan which is isolated and purified from nutmeg and the aril of nutmeg of the present invention for preparing reagent for inducing collagen synthesis or suppressing collagen degradation.

In addition, the present invention provides a method comprising administering or applying an effective amount of an extract of nutmeg, the aril of nutmeg and fragrin A, austobailignan 7, licarin E, and macelignan which is isolated and purified from nutmeg and the aril of nutmeg to a subject in need thereof for reducing wrinkle. Also, it provides a method comprising administering or applying an effective amount of an extract of nutmeg, the aril of nutmeg and fragrin A, austobailignan 7, licarin E, and macelignan which is isolated and purified from nutmeg and the aril of nutmeg to a subject in need thereof for inducing collagen synthesis or suppressing collagen degradation.

In the above, an extract of nutmeg, the aril of nutmeg and fragrin A, austobailignan 7, licarin E, and macelignan which is isolated and purified from nutmeg and the aril of nutmeg and their effects are well described above, and as used herein, the "effective amount" refers to the amount effective in reducing wrinkle, inducing collagen synthesis or suppressing collagen degradation in the subject for administration nutmeg, the aril of nutmeg and fragrin A, austobailignan 7, licarin E, and macelignan which is isolated and purified from nutmeg and the aril of nutmeg and the "subject" refers to mammals, particularly, animals comprising human. The subject may be patient in need of anti-wrinkle treatment.

An extract of nutmeg, the aril of nutmeg and fragrin A, austobailignan 7, licarin E, and macelignan which is isolated and purified from nutmeg and the aril of nutmeg of the present invention may be administered until desired effect among the said effects are derived, and can be administered by oral or parenteral ways which are well known in the art.

Advantageous Effects

As shown in the above, an extract of nutmeg, the aril of nutmeg and fragrin A, austobailignan 7, licarin E, and macelignan which is isolated and purified from nutmeg and the aril of nutmeg of the present invention suppresses collagen degradation enzyme-1 (MMP-1, matrix metalloproteinase-1) which is important in wrinkle formation and thereby suppresses collagen degradation and activated formation of new collagen (type-1 procollagen), and have improved effect on inhibiting wrinkle caused by photoaging. Accordingly, an extract of nutmeg, the aril of nutmeg and fragrin A, austobailignan 7, licarin E, and macelignan which is isolated and purified from nutmeg and the aril of nutmeg of the present invention may be useful for preventing or treating wrinkle caused by photoaging.

MODE FOR INVENTION

Hereinafter, the present invention will be described in detail by examples. It is to be understood, however, that these examples are for illustrative purpose only and are not constructed to limit the scope of the present invention.

EXAMPLE 1

Separation and Purification of Fragrin A and Austrobailignan-7 from Aril of Nutmeg and Determination of Structures Thereof <1-1> Separation and Purification of Fragrin A and Austrobailignan-7

Figure 1:
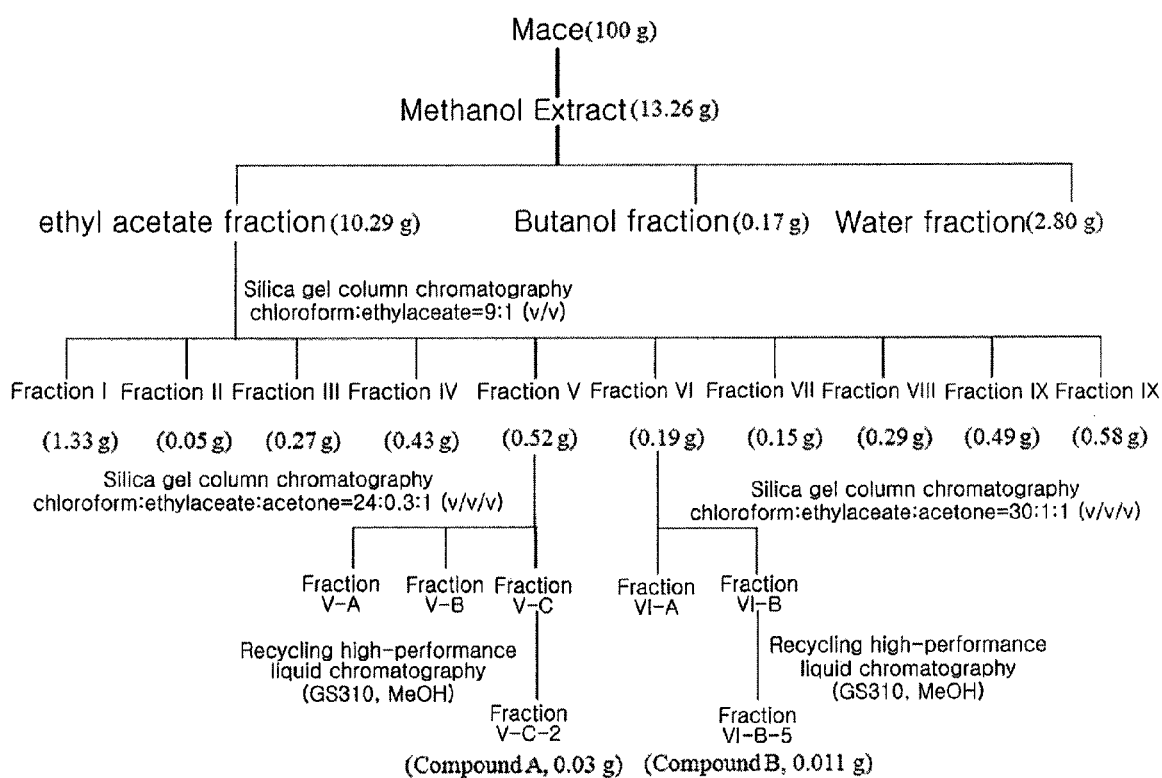
FIG. 1 shows isolation scheme of fragrin A and austobailignan 7 from the aril of nutmug.

100 g of the dried and ground aril of nutmeg was added to 400 ml of 75% methanol and left to stand at room temperature for 2 days. The extracted solution was filtered and concentrated in a vacuum, thus preparing 13.26 g of a 75% methanol extract of the aril of nutmeg. The extracted solution was fractionated with ethylacetate, butanol and water. The ethylacetate fraction (10.29 g) was eluted by silica gel column chromatography with a mixed solution of chloroform and ethylacetate (9:1 (v/v)) to obtain fraction V (0.52 g) and fraction VI (0.19 g). The fraction V was subjected to column chromatography with a mixed solvent of chloroform, ethylacetate and acetone (24:0.3:1 (v/v/v)) to obtain fraction V-C (0.05 g). Then, the fraction V-C was eluted by recycling high-performance liquid chromatography with 100% methanol to obtain single material fraction V-C-2 fragrin A (0.03 g). Also, the fraction VI was subjected to column chromatography with a mixed solvent of chloroform, ethylacetate and acetone (30:1:2 (v/v/v)) to obtain fraction VI-B (0.52 g). Then, the fraction VI-B was eluted by recycling high-performance liquid chromatography with 100% methanol to obtain single material fraction VI-B-5 austrobailignan-7 (0.011 g). This separation process is shown in FIG. 1.

<1-2> Structural Analysis of Single Material V-C-2

To determine the structure of the separated single material V-C-2, the $^1$H-NMR spectrum and $^{13}$C-NMR spectrum of the material were measured at 600 MHz and 150 MHz (solvent: CDCl$_3$), respectively. The results of comprehensive analysis of $^1$H-NMR and $^{13}$C-NMR are shown in Table 1 blow.

TABLE 1

| Position | 13C-NMR | 1H-NMR |
|---|---|---|
| 1 | 134.5 | |
| 2 | 112.4 | 6.77 (1H, d) |
| 3 | 146.3 | 3.82 (3H, s, 3-OMe) |
| 4 | 144.0 | 5.48 (1H, s, —OH) |
| 5 | 114.1 | 6.82 (1H, d) |
| 6 | 122.3 | 6.70 (1H, dd) |
| α | 43.0 | 2.72 (1H, dd) |
| | | 3.12 (1H, dd) |
| β | 79.8 | 4.33 (1H, dd) |
| γ | 19.6 | 1.20 (3H, d) |
| 1' | 135.6 | |
| 2' | 153.8 | 3.80 (6H, s) |
| 3' | 105.7 | 6.40 (2H, d', 5'-H) |
| 4' | 131.2 | |
| 5' | 105.7 | 6.40 (2H, 3', 5'-H) |
| 6' | 153.8 | 3.80 (6H, s, 2'-OMe, 6'-OMe) |
| α | 40.5 | 3.34 (2H, d) |
| β | 137.4 | 5.92-6.02 (1H, m) |
| γ | 115.8 | 5.07-5.15 (2H, m) |
| —OMe | 56.0 | |
| | 56.2 | |

In order to measure $^1$H-$^1$H correlation and $^1$H-$^{13}$C correlation on the basis of the results of the $^{13}$C-NMR spectrum and the $^1$H-NMR spectrum, the $^1$H-$^1$H COSY spectrum and the $^1$H-$^{13}$C HMBC spectrum were measured. The [M]$^+$ of the single material was observed at m/z 358 in FAB/MS, suggesting that the material had a molecular weight of 358 and a molecular formula of $C_{21}H_{26}O_5$.

Through the above results of $^1$H-NMR, $^{13}$C-NMR, $^1$H-$^1$H COSY, $^1$H-$^{13}$C HMBC and FAB/MS and the prior reference (*Chem. Pharm. Bull.*, 35: 668, 1987), the separated single material was found to be fragrin A, 2-(4-allyl-2,6-dimethoxyphenoxy)-1-(4-hydroxy-3-methoxyphenyl)-propane represented by the following formula 1:

<Formula 1>

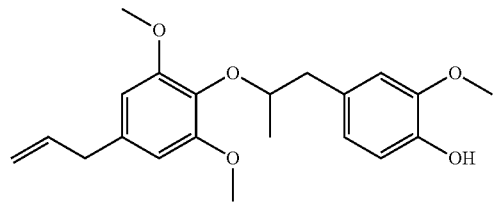

<1-3> Structural Analysis of Single Material VI-B-5

To determine the structure of the separated single material VI-B-5, the $^1$H-NMR spectrum and $^{13}$C-NMR spectrum of the single material were measured at 600 MHz and 150 MHz (solvent: CDCl$_3$). The results of comprehensive analysis of $^1$H-NMR and $^{13}$C-NMR are shown in Table 2 below.

TABLE 2

| Position | $^{13}$C-NMR | $^1$H-NMR |
|---|---|---|
| 1 | 137.4 | |
| 2 | 108.9 | 6.92 (1H, d) |
| 3 | 148.1 | |
| 4 | 147.1 | |
| 5 | 106.7 | 6.78 (1H, d) |
| 6 | 119.8 | 6.82 (1H, dd) |

TABLE 2-continued

| Position | $^{13}$C-NMR | $^1$H-NMR |
|---|---|---|
| α | 85.9 | 4.61 (1H, d) |
| β | 43.7 | 2.39-2.43 (2H, m) |
| γ | 12.0 | 1.00 (3H, d) |
| 1' | 132.7 | |
| 2' | 119.0 | 6.91 (1H, d) |
| 3' | 114.2 | |
| 4' | 144.5 | 5.54 (1H, s, —OH) |
| 5' | 146.5 | 6.88 (1H, d) |
| 6' | 108.2 | 6.77 (1H, dd) |
| α' | 85.0 | 5.42 (1H, d) |
| β' | 47.9 | 2.39-2.43 (2H, m) |
| γ' | 9.6 | 0.61 (3H, d) |
| —OMe | 56.2 | 3.89 (3H, s) |
| —OCH$_2$O— | 101.1 | 5.94 (1H, d) 5.95 (1H, d) |

To measure $^1$H-$^1$H correlation and $^1$H-$^{13}$C correlation on the basis of the results of the $^{13}$C-NMR spectrum and the $^1$H-NMR spectrum, the $^1$H-$^1$H COSY spectrum and the $^1$H-$^{13}$C HMBC spectrum were measured. The [M]$^+$ of the separated single material was observed at m/z 342 in FAB/MS, suggesting that the material had a molecular weight of 342 and a molecular formula of $C_{20}H_{22}O_5$.

Through the above results of $^1$H-NMR, $^{13}$C-NMR, $^1$H-$^1$H COSY, $^1$H-$^{13}$C HMBC and FAB/MS and the prior reference (*Aust. J. Chem.*, 28: 81, 1975), the separated single material was found to be austrobailignan-7 represented by the following formula 2:

<Formula 2>

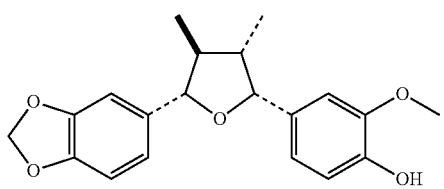

EXAMPLE 2

Cell Proliferation Effect

In order to examine a cell proliferation effect proving the effect of reducing skin wrinkles, an MTT assay (3-(4,5-dimethylthiazol-2-yl)-2,5-diphenyl tetrazolium bromide reduction method) was carried out using fibroblasts.

First, human normal fibroblasts were plated into a 96-well plate at a concentration of 2×10$^5$ cells/well and primarily cultured in 10% FBS (fetal bovine serum)-containing DMEM medium in conditions of 37° C. and 5% CO$_2$ for 24 hours. After the primary culture, the cells were treated with varying concentrations of the inventive sample. Then, the medium was replaced with a serum-free medium, and the cells were secondarily cultured for 48 hours. After the secondary culture step, 100 μl of MTT solution was added to the medium. Then, the resulting solution was left to stand for 4 hours, and then the medium was removed. 100 μl of dimethyl sulfoxide solution was added to each well and stirred for 20 minutes, and then the absorbance of each well at 540 nm was measured with a microplate reader.

TEST EXAMPLE 1

Cell Proliferation Effects of Fragrin A and Austobailignan 7

According to the method of Example 2, the cell proliferation effects of 75% methanol extract of the aril of nutmeg and fragrin A and austobailignan 7 which are isolated and purified thereof were measured. In the MTT assay, a culture medium not treated with the sample was used as a control group and measured for absorbance, and the analysis results are shown in Table 3 below.

TABLE 3

| Concentration (μg/ml) | Proliferation effect (%) 75% methanol extract of the aril of nutmeg | Proliferation effect (%) fragrin A | Proliferation effect (%) austobailignan 7 |
|---|---|---|---|
| 3 | 103 | 101 | 104 |
| 5 | 102 | 104 | 105 |
| 10 | 106 | 108 | 110 |

As can be seen in Table 3, the extract of the aril of nutmeg, fragrin A and austobailignan 7 of the present invention had excellent cell proliferation effects compared to those of the comparative groups.

EXAMPLE 3

Measurement of Matrix Metalloproteinase-1 (MMP-1) in Fibroblasts Radiated With UV Light Fibroblasts were cultured in a 60-mm dish at a concentration of 2×10$^5$ cells/ml to a confluence of about 85%. Before UV radiation, the medium was removed, and the cells were washed with PBS to remove a serum component therefrom, and then radiated with UV light at a dose of 20 J/cm$^2$. After the fibroblast cells were radiated with UV light, the cells were treated with each of the samples and cultured with serum free DMEM for 48 hours.

In order to measure the expression levels of matrix metalloproteinase-1 (MMP-1), Western blot was used, and the amount of total protein in the medium containing the fibroblasts cultured therein was quantified using the Bradford method.

The extracted protein was electrophoresed on 10% SDS-polyacrylamide gel, and then transferred to a nitrocellulose membrane. The membrane was blocked with 5% skim milk at room temperature for 1 hour in order to prevent it from being contaminated with other unknown proteins. Primary antibody to matrix metalloproteinase-1 was diluted in a blocking solution at a ratio of 1:1000 and allowed to react with the membrane at room temperature for 2 hours. After the primary antibody reaction, the membrane was washed three times with Tris-buffer saline Tween 20 (TBST) with shaking for 10 minutes each time. Secondary antibodies recognizing the primary antibodies to matrix metalloproteinase-1 was diluted in 5% skim milk at a ratio of 1:1000 and allowed to react with the membrane at room temperature for 1 hour. Then, the membrane was washed three times with tris-buffer saline Tween 20 with shaking for 10 minutes each time in the same manner as in the case of the primary antibody reaction, and then was developed by chemiluminescence.

TEST EXAMPLE 2

Measurement of Expression Levels of Matrix Metalloproteinase-1 (MMP-1) in Cells when Treated with an Extract of the Aril of the Nutmeg In order to measure the matrix metalloproteinase-1 (MMP-1) inhibitory activity effect of 75% methanol extract of the aril of the nutmeg, the expression levels of matrix metalloproteinase-1 (MMP-1) were analyzed using the Western blot assay of Example 3. For a result, they were compared that the testing group which was treated with an extract of the aril of the nutmeg in different concentration (3, 5 and 10 µg/ml), the negative group which was treated with 0.01% of dimethyl sulfoxide and positive grouped which was treated with 0.01% of dimethyl sulfoxide and 20 J/cm$^2$ of UV together.

Figure 2:
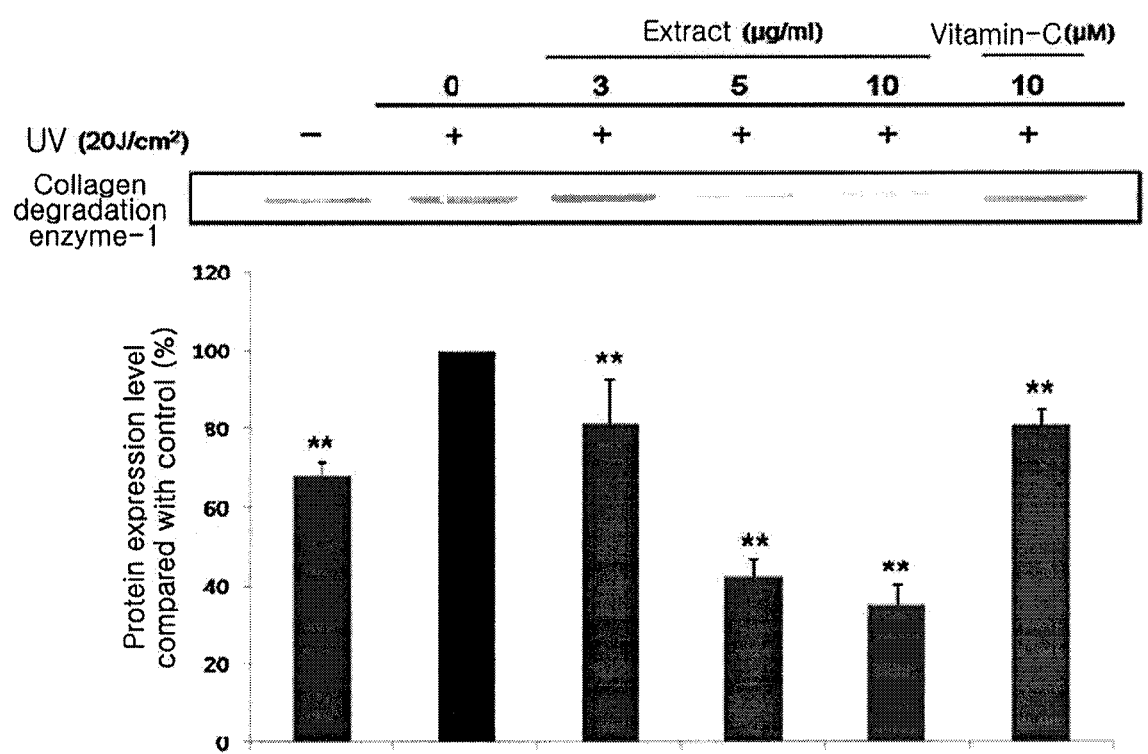
FIG. 2 is a graph showing suppress activity of collagen degradation enzyme-1 by 75% methanol extract of the aril of nutmug.

As a result, as shown in FIG. 2, the extract of the aril of the nutmeg inhibited the expression of matrix metalloproteinase-1 with dose-dependent manners, and in every treated concentration, it showed significant difference (**, p<0.01; *, p<0.05) compared with positive control which is treated with 20 J/cm$^2$ of UV. For example, when each is treated with 10 µg/ml, inhibition of expression of matrix metalloproteinase-1 for vitamin-C which is a comparative compound, is 20% higher than the negative control and in case of the extract of the aril of the nutmeg of the present invention, it is 60%. Accodingly, the inventor confirmed that the extract of the aril of the nutmeg of the present showed similar activity to vitamin-C which is well known as antiaging compound, thereby inhibit expression of matrix metalloproteinase-1 effectively, and the extract of the aril of the nutmeg of the present invention showed the effect on inhibiting expression of matrix metalloproteinase-1 which is marker of antiaging, either.

TEST EXAMPLE 3

Measurement of Expression Levels of Matrix Metalloproteinase-1 (MMP-1) in Cells when Treated with Fragrin A In order to measure the matrix metalloproteinase-1 (MMP-1) inhibitory activity effect of fragrin A, they were compared that the testing group which was treated with fragrin A in different concentration (3, 5 and 100M), the negative group which was treated with 0.01% of dimethyl sulfoxide and positive group which was treated with 0.01% of dimethyl sulfoxide and 20 J/cm$^2$ of UV together.

Figure 3:
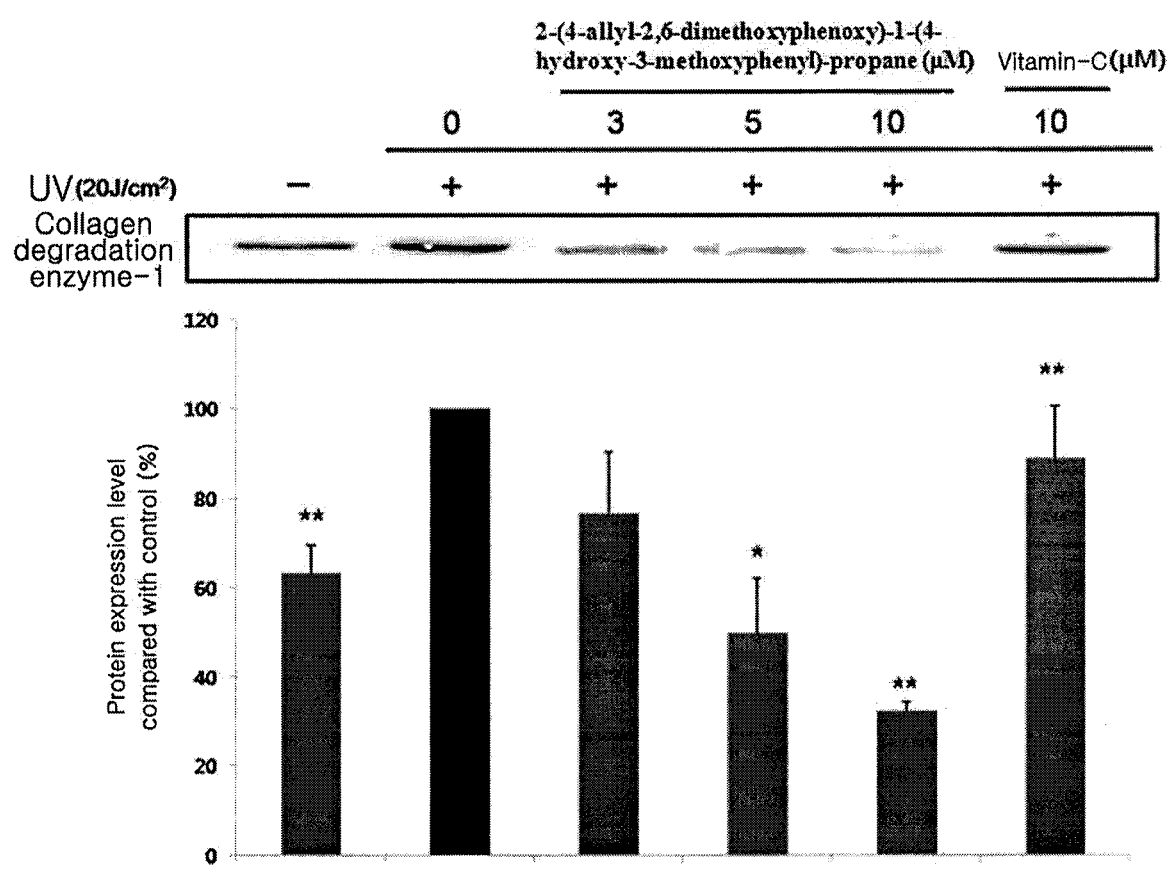
FIG. 3 is a graph showing suppress activity of collagen degradation enzyme-1 by fragrin A.

As a result, as shown in FIG. 3, fragrin A inhibited the expression of matrix metalloproteinase-1 with dose-dependent manners, and in every treated concentration, it showed significant difference (**, p<0.01; *, p<0.05) compared with positive control which is treated with 20 J/cm$^2$ of UV. For example, when each is treated with 10 µM, inhibition of expression of matrix metalloproteinase-1 for vitamin-C which is a comparative compound, is 20% higher than the negative control and in case of fragrin A of the present invention, it is 65%. Accodingly, the inventor confirmed that fragrin A of the present invention showed similar activity to vitamin-C which is well known as antiaging compound, thereby inhibit expression of matrix metalloproteinase-1 effectively, and fragrin A of the present invention showed the effect on inhibiting expression of matrix metalloproteinase-1 which is marker of antiaging, either.

TEST EXAMPLE 4

Measurement of Expression Levels of Matrix Metalloproteinase-1 (MMP-1) in Cells when Treated with Austobailignan 7

In order to measure the matrix metalloproteinase-1 (MMP-1) inhibitory activity effect of austobailignan 7, they were compared that the testing group which was treated with fragrin A in different concentration (3, 5 and 10 µM), the negative group which was treated with 0.01% of dimethyl sulfoxide and positive grouped which was treated with 0.01% of dimethyl sulfoxide and 20 J/cm$^2$ of UV together.

Figure 4:
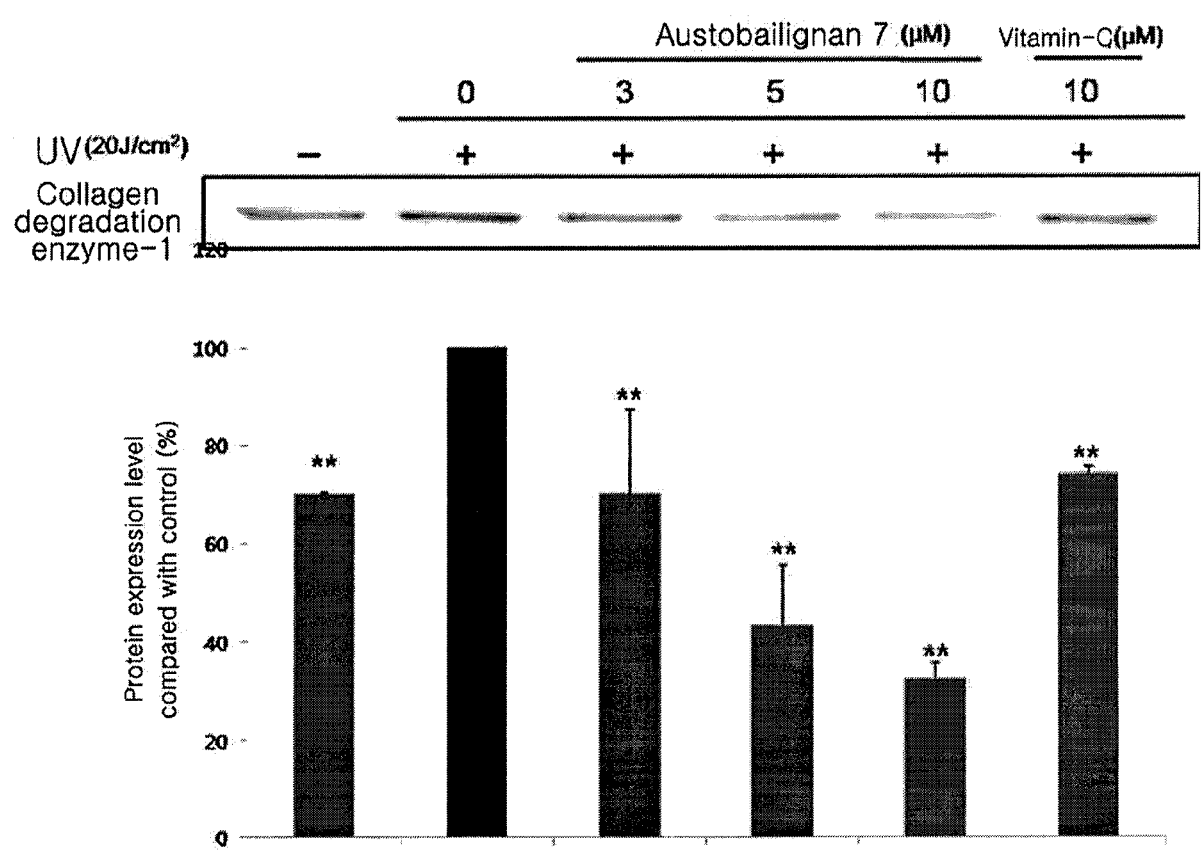
FIG. 4 is a graph showing suppress activity of collagen degradation enzyme-1 by austobailignan 7.

As a result, as shown in FIG. 4, austobailignan 7 inhibited the expression of matrix metalloproteinase-1 with dose-dependent manners, and in every treated concentration, it showed significant difference (**, p<0.01; *, p<0.05) compared with positive control which is treated with 20 J/cm$^2$ of UV. For example, when each is treated with 10 µM, inhibition of expression of matrix metalloproteinase-1 for vitamin-C which is a comparative compound, is 20% higher than the negative control and in case of austobailignan 7 of the present invention, it is 65%. Accordingly, the inventor confirmed that austobailignan 7 of the present invention showed similar activity to vitamin-C which is well known as antiaging compound, thereby inhibit expression of matrix metalloproteinase-1 effectively, and austobailignan 7 of the present invention showed the effect on inhibiting expression of matrix metalloproteinase-1 which is marker of antiaging, either.

EXAMPLE 4

Measurement of Expression Levels of Matrix Metalloproteinase-1 (MMP-1) in Cells when Treated with Ethanol Extract of the Aril of the Nutmeg 100 g of the dried and ground aril of nutmeg was added to 400 ml of ethanol and left to stand at room temperature for 2 days. The extracted solution was filtered and concentrated in a vacuum, thus preparing 13.98 g of a ethanol extract of the aril of nutmeg.

Concerning the above ethanol extract, measurement of expression levels of matrix metalloproteinase-1 (MMP-1) was performed as shown in Example 3 and then as a result, the expression levels of matrix metalloproteinase-1 (MMP-1) of the group which was treated with 10 µg/ml of ethanol extract decreased 65% than positive control group which was treated with 20 J/cm$^2$ of UV.

EXAMPLE 5

Measurement of Expression Levels of Matrix Metalloproteinase-1 (MMP-1) in Cells when Treated with Hexane Extract of the Aril of the Nutmeg 100 g of the dried and ground aril of nutmeg was added to 400 ml of hexane and left to stand at room temperature for 2 days. The extracted solution was filtered and concentrated in a vacuum, thus preparing 16.73 g of a hexane extract of the aril of nutmeg.

Concerning the above extract, measurement of expression levels of matrix metalloproteinase-1 (MMP-1) was performed as shown in Example 3 and then as a result, the expression levels of matrix metalloproteinase-1 (MMP-1) of the group which was treated with 10 µg/ml of hexane extract decreased 55% than positive control group which was treated with 20 J/cm$^2$ of UV.

EXAMPLEs 6 to 9

Preparation of Lotions Containing Antiaging and Wrinkle Reducing Composition of the Present Invention The ethanol extract of the aril of the nutmeg of Example 4 was used to prepare lotions having compositions of Examples 6 to 9.

The extract was dissolved in ethanol at concentrations of 10.0 wt %, 1.0 wt %, 0.1 wt % and 0.01 wt %, and the weight thereof was adjusted with ethanol. Then, the solution was uniformly stirred (Table 4).

TABLE 4

| component | Example 6 | Example 7 | Example 8 | Example 9 |
|---|---|---|---|---|
| 1. ethanol extract (%) | 10.0 | 1.0 | 0.1 | 0.01 |
| 2. glycerin (%) | 2.0 | 2.0 | 2.0 | 2.0 |
| 3. prolyleneglycol (%) | 2.0 | 2.0 | 2.0 | 2.0 |
| 4. potassium phosphate (%) | 0.1 | 0.1 | 0.1 | 0.1 |
| 5. sodium phosphate dibasic (%) | 0.05 | 0.05 | 0.05 | 0.05 |
| 6. fragrance (%) | 0.02 | 0.02 | 0.02 | 0.02 |
| 7. ethanol (96%)(%) | 20 | 20 | 20 | 20 |
| 8. Purified water (%) | balance | balance | balance | balance |
| 9. Preservative (%) | qs | qs | qs | qs |

EXAMPLEs 10 to 13

Preparation of Creams Containing an Extract of the Aril of the Nutmeg

The ethanol extract of the aril of the nutmeg of Example 4 was used to prepare creams having compositions of Examples 10 to 13. First, materials (2)-(6) were dissolved at 75-80° C., and materials (7)-(10) were dissolved at the same temperature. The materials (7)-(10) were emulsified in the materials (2)-(6), and then the crude extract was added thereto at each of concentrations of 10.0 wt %, 1.0 wt %, 0.1 wt % and 0.01%, and the emulsions were stirred. Finally, fragrance was added thereto and the balance of purified water was added.

TABLE 5

| component | Example 10 | Example 11 | Example 12 | Example 13 |
|---|---|---|---|---|
| 1. ethanol extract (%) | 10.0 | 1.0 | 0.1 | 0.01 |
| 2. glycerin | 2.0 | 2.0 | 2.0 | 2.0 |
| 3. propyleneglycol | 2.0 | 2.0 | 2.0 | 2.0 |
| 4. chlorolauryl sulfide | 8.0 | 8.0 | 8.0 | 8.0 |
| 5. stearin | 5.4 | 5.4 | 5.4 | 5.4 |
| 6. mineral oil | 4.5 | 4.5 | 4.5 | 4.5 |
| 7. fragrance | 0.02 | 0.02 | 0.02 | 0.02 |
| 8. cetyl alcohol | 6.5 | 6.5 | 6.5 | 6.5 |
| 9. purified water | balance | balance | balance | balance |
| 10. preservative | qs | qs | qs | qs |

EXAMPLEs 14 to 17

Preparation of Lotions Containing Fragrin A

Fragrin A of the present invention was used to prepare lotions having compositions of Examples 14 to 17. Fragrin A was dissolved in water at 4 concentrations of 5.0 wt %, 0.1 wt %, 0.01 wt %, and 0.001 wt % and mixed with phosphoric acid solution. The solution was mixed with ethanol, glycerin, propyleneglycol and added fragrance and preservative, and then, the weight thereof was adjusted with water. Then, the solution was uniformly stirred (Table 6).

TABLE 6

| component | Example 14 | Example 15 | Example 16 | Example 17 |
|---|---|---|---|---|
| 1. fragrin A (%) | 5.0 | 0.1 | 0.01 | 0.001 |
| 2. glycerin (%) | 2.0 | 2.0 | 2.0 | 2.0 |
| 3. prolyleneglycol (%) | 2.0 | 2.0 | 2.0 | 2.0 |
| 4. potassium phosphate (%) | 0.1 | 0.1 | 0.1 | 0.1 |
| 5. sodium phosphate dibasic (%) | 0.05 | 0.05 | 0.05 | 0.05 |
| 6. fragrance (%) | 0.02 | 0.02 | 0.02 | 0.02 |
| 7. ethanol (96%)(%) | 20 | 20 | 20 | 20 |
| 8. Purified water (%) | balance | balance | balance | balance |
| 9. Preservative (%) | qs | qs | qs | qs |

EXAMPLEs 18 to 21

Preparation of Creams Containing an Fragrin A

Fragrin A of the present invention was used to prepare creams having compositions of Examples 18 to 21. First, materials (2)-(6) were dissolved at 75-80 t, and materials (7)-(10) were dissolved at the same temperature. The materials (7)-(10) were emulsified in the materials (2)-(6), and then fragrin A was added thereto at each of concentrations of 5.0 wt %, 0.1 wt % 0.01% and 0.001% and the emulsions were stirred. Finally, fragrance was added thereto and the balance of purified water was added (Table 7).

TABLE 7

| component | Example 18 | Example 19 | Example 20 | Example 21 |
|---|---|---|---|---|
| 1. fragrin A (%) | 5.0 | 0.1 | 0.01 | 0.001 |
| 2. glycerin | 2.0 | 2.0 | 2.0 | 2.0 |
| 3. propyleneglycol | 2.0 | 2.0 | 2.0 | 2.0 |
| 4. chlorolauryl sulfide | 8.0 | 8.0 | 8.0 | 8.0 |
| 5. stearin | 5.4 | 5.4 | 5.4 | 5.4 |
| 6. mineral oil | 4.5 | 4.5 | 4.5 | 4.5 |
| 7. fragrance | 0.02 | 0.02 | 0.02 | 0.02 |
| 8. cetyl alcohol | 6.5 | 6.5 | 6.5 | 6.5 |
| 9. purified water | balance | balance | balance | balance |
| 10. preservative | qs | qs | qs | qs |

EXAMPLEs 22 to 25

Preparation of Lotions Containing Austobailignan 7

Austobailignan 7 of the present invention was used to prepare lotions having compositions of Examples 22 to 25. Austobailignan 7 was dissolved in water at 4 concentrations of 5.0 wt %, 0.1 wt %, 0.01 wt %, and 0.001 wt % and mixed with phosphoric acid solution. The solution was mixed with ethanol, glycerin, propyleneglycol and added fragrance and preservative, and then, the weight thereof was adjusted with water. Then, the solution was uniformly stirred (Table 8).

TABLE 8

| component | Example 22 | Example 23 | Example 24 | Example 25 |
|---|---|---|---|---|
| 1. austobailignan 7 (%) | 5.0 | 0.1 | 0.01 | 0.001 |
| 2. glycerin(%) | 2.0 | 2.0 | 2.0 | 2.0 |
| 3. prolyleneglycol(%) | 2.0 | 2.0 | 2.0 | 2.0 |
| 4. potassium phosphate (%) | 0.1 | 0.1 | 0.1 | 0.1 |
| 5. sodium phosphate dibasic (%) | 0.05 | 0.05 | 0.05 | 0.05 |
| 6. fragrance (%) | 0.02 | 0.02 | 0.02 | 0.02 |
| 7. ethanol(96%)(%) | 20 | 20 | 20 | 20 |
| 8. Purified water(%) | balance | balance | balance | balance |
| 9. Preservative (%) | qs | qs | qs | qs |

EXAMPLEs 26 to 29

Preparation of Creams Containing an Austobailignan 7

Austobailignan 7 of the present invention was used to prepare creams having compositions of Examples 26 to 29. First, materials (2)-(6) were dissolved at 75-80 r, and materials (7)-(10) were dissolved at the same temperature. The materials (7)-(10) were emulsified in the materials (2)-(6), and then Austobailignan 7 was added thereto at each of concentrations of 5.0 wt %, 0.1 wt % 0.01% and 0.001% and the emulsions were stirred. Finally, fragrance was added thereto and the balance of purified water was added (Table 9).

TABLE 9

| component | Example 26 | Example 27 | Example 28 | Example 29 |
|---|---|---|---|---|
| 1. Austobailignan 7 (%) | 5.0 | 0.1 | 0.01 | 0.001 |
| 2. glycerin | 2.0 | 2.0 | 2.0 | 2.0 |
| 3. propyleneglycol | 2.0 | 2.0 | 2.0 | 2.0 |
| 4. chlorolauryl sulfide | 8.0 | 8.0 | 8.0 | 8.0 |
| 5. stearin | 5.4 | 5.4 | 5.4 | 5.4 |
| 6. mineral oil | 4.5 | 4.5 | 4.5 | 4.5 |
| 7. fragrance | 0.02 | 0.02 | 0.02 | 0.02 |
| 8. cetyl alcohol | 6.5 | 6.5 | 6.5 | 6.5 |
| 9. purified water | balance | balance | balance | balance |
| 10. preservative | qs | qs | qs | qs |

TEST EXAMPLE 4

In Vivo Measurement of Collagen Synthesis of Extract of the Aril of the Nutmeg-Containing Composition Hairless mice were radiated with UV light at a dose of 20 J/cm² one time everyday for 4 weeks, and then 100 ml of each of extract of the aril of the nutmeg-containing compositions of Examples 6 to 13 was applied to the back of the mice. Then, the mice were biopsied, and the formation of collagen in the biopsied tissue was histologically measured. Herein, the measurement of the amount of newly produced collagen was carried out by immunostaining the tissue and subjecting the immunostained tissue to image analysis. The measurement results are shown in Table 10 below.

TABLE 10

| Result | Increase (%) in collagen |
|---|---|
| Control | 0 |
| Lotion Example 6 | 34.8 |
| Lotion Example 7 | 21.2 |
| Lotion Example 8 | 8.4 |
| Lotion Example 9 | 35 |
| Control | 0 |
| Cream Example 10 | 35.7 |
| Cream Example 11 | 23.1 |
| Cream Example 12 | 10.2 |
| Cream Example 13 | 4.1 |

As can be seen in Table 10, the increase in the content of the aril of the nutmeg ethanol extract led to the increase in collagen synthesis, and the activity of the extract was higher in the creams than in the lotions. This is believed to be because the retention of the creams in the skin is higher than that of the lotions.

TEST EXAMPLE 5

In Vivo Measurement of Collagen Synthesis of Fragrin A-Containing Composition

Hairless mice were radiated with UV light at a dose of 20 J/cm² one time everyday for 4 weeks, and then 100 ml of each of fragrin A-containing compositions of Examples 14 to 21 was applied to the back of the mice. Then, the mice were biopsied, and the formation of collagen in the biopsied tissue was histologically measured. Herein, the measurement of the amount of newly produced collagen was carried out by immunostaining the tissue and subjecting the immunostained tissue to image analysis. The measurement results are shown in Table 11 below.

TABLE 11

| Result | Increase (%) in collagen |
|---|---|
| Control | 0 |
| Lotion Example 14 | 75.4 |
| Lotion Example 15 | 32.7 |
| Lotion Example 16 | 18.3 |
| Lotion Example 17 | 8.9 |
| Control | 0 |
| Cream Example 18 | 77.6 |
| Cream Example 19 | 38.1 |
| Cream Example 20 | 20.8 |
| Cream Example 21 | 9.0 |

As can be seen in Table 11, the increase in fragrin A led to the increase in collagen synthesis, and the activity of the extract was higher in the creams than in the lotions. This is believed to be because the retention of the creams in the skin is higher than that of the lotions.

TEST EXAMPLE 6

In Vivo Measurement of Collagen Synthesis of Austobailignan 7-Containing Composition Hairless mice were radiated with UV light at a dose of 20 J/cm² one time everyday for 4 weeks, and then 100 ml of each of austobailignan 7-containing compositions of Examples 22 to 29 was applied to the back of the mice. Then, the mice were biopsied, and the formation of collagen in the biopsied tissue was histologically measured. Herein, the measurement of the amount of newly produced collagen was carried out by immunostaining the tissue and subjecting the immunostained tissue to image analysis. The measurement results are shown in Table 12 below.

TABLE 12

| Result | Increase (%) in collagen |
|---|---|
| Control | 0 |
| Lotion Example 14 | 68.7 |
| Lotion Example 15 | 30.4 |
| Lotion Example 16 | 16.1 |
| Lotion Example 17 | 7.9 |
| Control | 0 |
| Cream Example 18 | 70.1 |
| Cream Example 19 | 36.3 |
| Cream Example 20 | 18.8 |
| Cream Example 21 | 8.5 |

As can be seen in Table 12, the increase in austobailignan 7 led to the increase in collagen synthesis, and the activity of the extract was higher in the creams than in the lotions. This is believed to be because the retention of the creams in the skin is higher than that of the lotions.

EXAMPLE 30

Separation and Purification of Licarin E from Aril of Nutmeg

Figure 5:
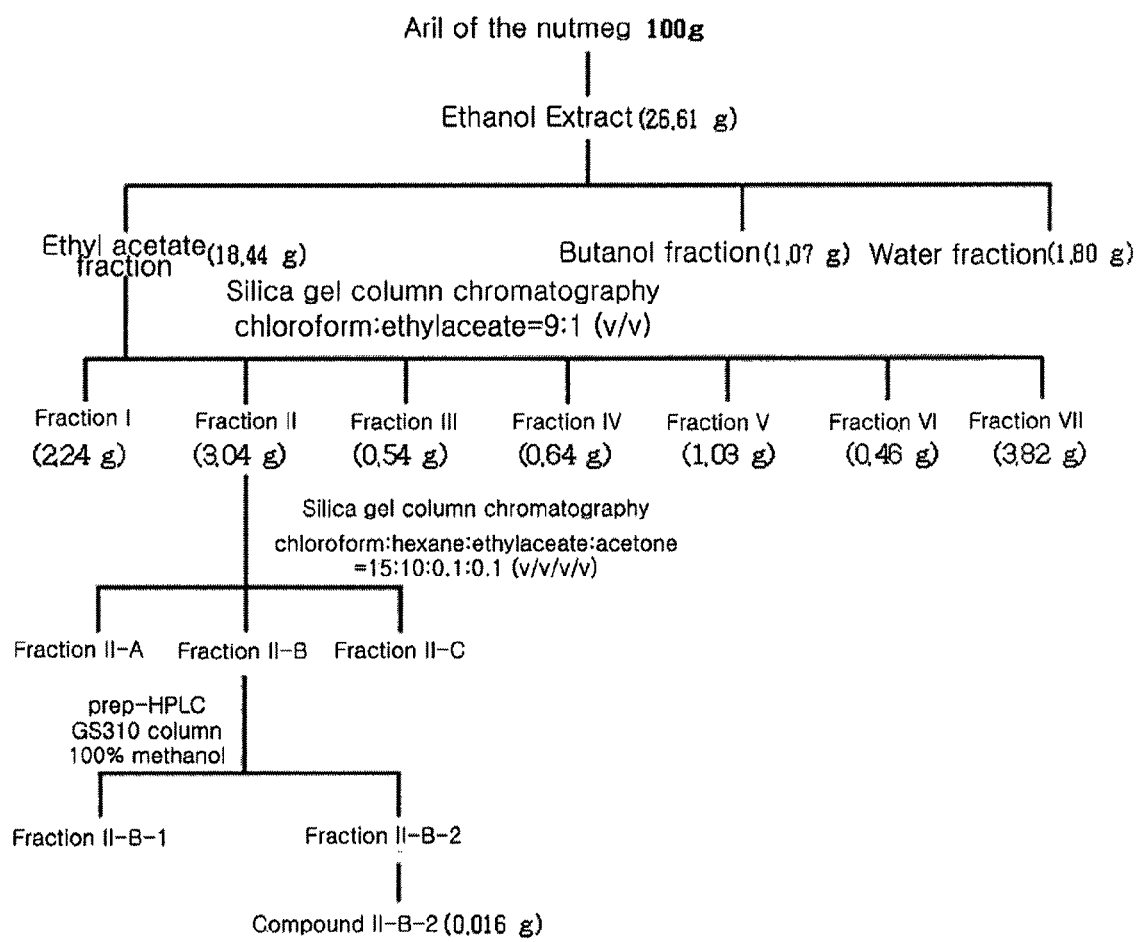
FIG. 5 shows isolation scheme of Licarin E from the aril of nutmug.

<30-1> Separation and Purification of Licarin E 100 g (dired weight) of the dried and ground aril of nutmeg was added to 400 ml of 95 v/v % ethanol and left to stand at room temperature for 2 days. The extracted solution was filtered twice with Whatman paper No. 2. Then, the ethanol filtered solution was concentrated in a vacuum and lyophilized, thus preparing 26.61 g of a crude ethanol extract of the aril of nutmeg. The extract was fractionated with ethylacetate, butanol and water in order. The ethylacetate fraction (18.44 g) was gained. It was eluted by silica gel column chromatography (Merck Kieselgel 66; 70-230 mesh) with a mixed solution of chloroform and ethylacetate (9:1 (v/v)) to obtain fraction II (3.04 g). The solvent was eliminated thoroughly by using the vacuum rotating concentrator, then preparing a crude ethanol extract of the aril of nutmeg. After that, the fraction II was subjected to column chromatography with a mixed solvent of chloroform, hexane, ethylacetate and acetone (15:10:0.1:0.1 (v/v/v/v)) to obtain fraction II-B. Then, the fraction II-B was eluted by preparative high-performance liquid chromatography with 100% methanol to obtain single material fraction II-B-2 (0.016 g). This separation process is shown in FIG. 5.

<30-2> Structural Analysis

To determine the structure of the separated single material II-B-2, the $^1$H-NMR spectrum and $^{13}$C-NMR spectrum of the material were measured at 600 MHz and 150 MHz (solvent: DMSO), respectively and DEPT spectrum were measured. The results of comprehensive analysis of $^1$H-NMR and $^{13}$C-NMR are shown in Table 13 blow.

TABLE 13

| Carbon No. | $\delta_C$ | $\delta_H$ |
|---|---|---|
| 1 | | |
| 2 | 93.0 | |
| 3 | 45.5 | 1.35 (3H, d, 7-OMe) |
| 3a | 132.7 | 5.48 (1H, s, —OH) |
| 4 | 113.0 | 6.82 (1H, d) |
| 5 | 131.8 | 6.70 (1H, dd) |

TABLE 13-continued

| Carbon No. | $\delta_C$ | $\delta_H$ |
|---|---|---|
| 6 | 109.2 | 5.15 (d, 9) |
| 7 | 143.7 | 3.2-3.7 (m) |
| 7a | 146.2 | 1.35 (3H, d, 7) |
| 3-Me | 17.6 | 5.92 |
| OMe | 55.7 | |
| 1' | 134.0 | |
| 2' | 106.3 | 3.80 (6H, s) |
| 3' | 147.5 | 3.88 (s) |
| 4' | 147.2 | |
| 5' | 107.7 | 6.40 (2H, 3', 5'-H) |
| 6' | 119.7 | 3.80 (6H, s, 2'-OMe, 6'-OMe) |
| α | 130.6 | 3.34 (2H, d) |
| β | 122.9 | 5.92-6.02 (1H, m) |
| γ | 18.1 | 1.84 (3H, d, 5) |

<30-3> Mass Analysis

In order to analyse the mass of the single material, FAB/MS was measured, and the [M]$^+$ of the single material was observed at m/z 324 in FAB/MS, suggesting that the material had a molecular weight of 324 and a molecular formula of $C_{20}H_{20}O_4$.

Through the above results of $^1$H-NMR, $^{13}$C-NMR, DEPT, and FAB/MS and the prior reference (Harvey D. J., J. Chromatogr., 110:91-102, 1975), the separated single material was found to be ligarin E represented by the following formula 3:

<Formula 3>

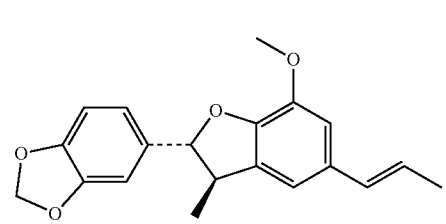

TEST EXAMPLE 7

Measurement of Expression Levels of Matrix Metalloproteinase-1 (MMP-1) in Cells when Treated with Licarin E In order to measure the matrix metalloproteinase-1 (MMP-1) inhibitory activity effect of licarin E, they were compared that the testing group which was treated with licarin E in different concentration of 3, 5 and 10 μM by using western blot method of Example 3, and as a result, they showed matrix metalloproteinase-1 (MMP-1) inhibitory activity effect of 35%, 47%, and 73%, respectively compared with UV 20 J/cm$^2$ treated positive control group.

This means licarin E of the present invention showed the effect on inhibiting expression of matrix metalloproteinase-1 which is marker of antiaging.

EXAMPLEs 31 to 34

Preparation of Lotions Containing Licarin E

Licarin E of the present invention was used to prepare lotions having compositions of Examples 31 to 34. Licarin E was dissolved in water at 4 concentrations of 5.0 wt %, 0.1 wt %, 0.01 wt %, and 0.001 wt % and mixed with phosphoric acid solution. The solution was mixed with ethanol, glycerin, propyleneglycol and added fragrance and preservative, and then, the weight thereof was adjusted with water. Then, the solution was uniformly stirred (Table 14).

TABLE 14

| component | Example 31 | Example 32 | Example 33 | Example 34 |
|---|---|---|---|---|
| 1. licarin E (%) | 5.0 | 0.1 | 0.01 | 0.001 |
| 2. glycerin(%) | 2.0 | 2.0 | 2.0 | 2.0 |
| 3. propyleneglycol(%) | 2.0 | 2.0 | 2.0 | 2.0 |
| 4. potassium phosphate (%) | 0.1 | 0.1 | 0.1 | 0.1 |
| 5. sodium phosphate dibasic (%) | 0.05 | 0.05 | 0.05 | 0.05 |
| 6. fragrance (%) | 0.02 | 0.02 | 0.02 | 0.02 |
| 7. ethanol(96%)(%) | 20 | 20 | 20 | 20 |
| 8. Purified water(%) | balance | balance | balance | balance |
| 9. Preservative (%) | qs | qs | qs | qs |

EXAMPLEs 35 to 38

Preparation of Creams Containing Licarin E

Licarin E of the present invention was used to prepare creams having compositions of Examples 35 to 38. First, materials (2)-(6) were dissolved at 75-80 r, and materials (7)-(10) were dissolved at the same temperature. The materials (7)-(10) were emulsified in the materials (2)-(6), and then licarin E was added thereto at each of concentrations of 5.0 wt %, 0.1 wt % 0.01% and 0.001% and the emulsions were stirred. Finally, fragrance was added thereto and the balance of purified water was added (Table 15).

TABLE 15

| component | Example 35 | Example 36 | Example 37 | Example 38 |
|---|---|---|---|---|
| 1. licarin E (%) | 5.0 | 0.1 | 0,01 | 0.001 |
| 2. glycerin | 2.0 | 2.0 | 2.0 | 2.0 |
| 3. propyleneglycol | 2.0 | 2.0 | 2.0 | 2.0 |
| 4. chlorolauryl sulfide | 8.0 | 8.0 | 8.0 | 8.0 |
| 5. stearin | 5.4 | 5.4 | 5.4 | 5.4 |
| 6. mineral oil | 4.5 | 4.5 | 4.5 | 4.5 |
| 7. fragrance | 0.02 | 0.02 | 0.02 | 0.02 |
| 8. cetyl alcohol | 6.5 | 6.5 | 6.5 | 6.5 |
| 9. purified water | balance | balance | balance | balance |
| 10. preservative | qs | qs | qs | qs |

TEST EXAMPLE 8

In Vivo Measurement of Collagen Synthesis of Licarin E-Containing Composition

Hairless mice were radiated with UV light (20 J/cm$^2$) one time everyday for 4 weeks, and then 100 ml of each of licarin E-containing compositions of Examples 31 to 38 was applied to the back of the mice. Then, the mice were biopsied, and the formation of collagen in the biopsied tissue was histologically measured. Herein, the measurement of the amount of newly produced collagen was carried out by immunostaining the tissue and subjecting the immunostained tissue to image analysis. The measurement results are shown in Table 16 below.

TABLE 16

| Result | Increase (%) in collagen |
|---|---|
| Control | 0 |
| Lotion Example 31 | 73.4 |
| Lotion Example 32 | 31.6 |
| Lotion Example 33 | 17.9 |
| Lotion Example 34 | 8.5 |
| Control | 0 |
| Cream Example 35 | 77.2 |
| Cream Example 36 | 38.0 |
| Cream Example 37 | 19.6 |
| Cream Example 38 | 8.9 |

As can be seen in Table 16, the increase in licarin E led to the increase in collagen synthesis, and the activity of the extract was higher in the creams than in the lotions. This is believed to be because the retention of the creams in the skin is higher than that of the lotions.

EXAMPLE 39

Separation and Purification of Macelignan from *Myristica fragrans*

Figure 6:
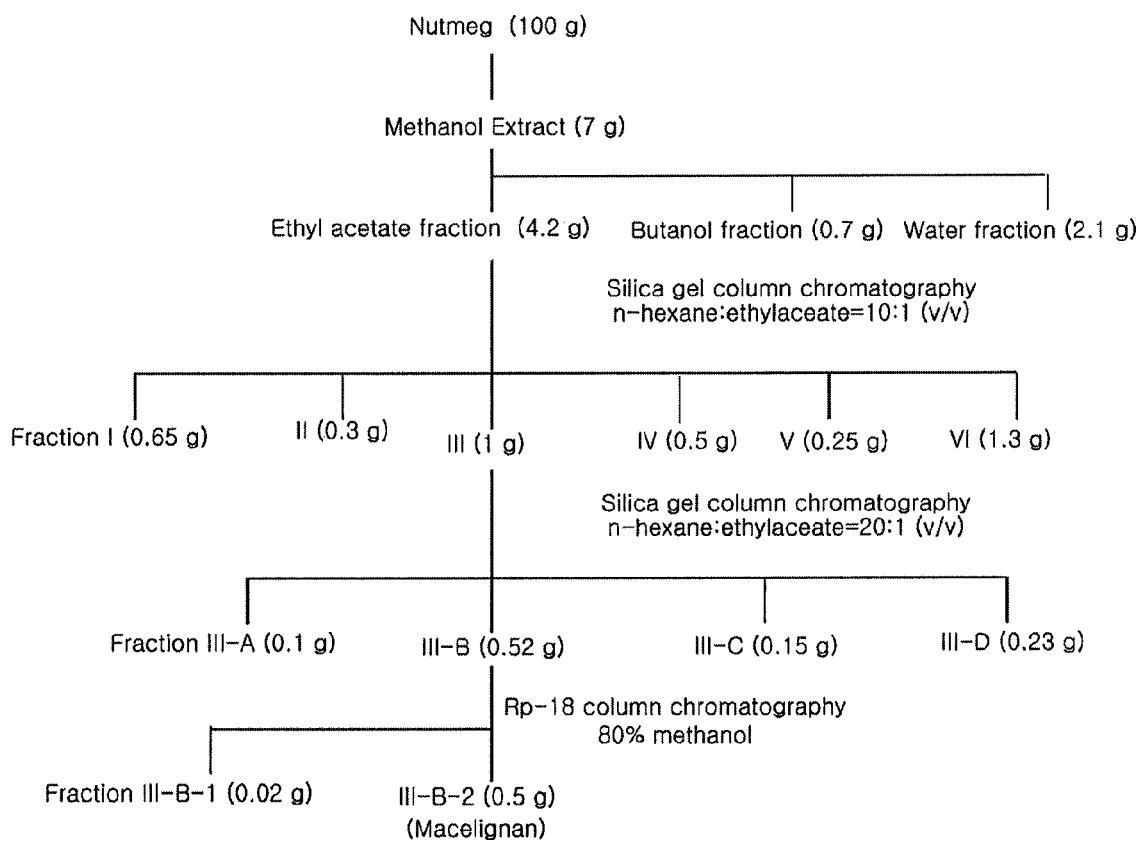
FIG. 6 shows isolation scheme of macelignan from the nutmug.

<39-1> Separation and Purification of Macelignan 100 g (dired weight) of the dried and ground nutmeg was added to 400 ml of 75% methanol and left to stand at room temperature for 2 days. The extracted solution was filtered and concentrated in a vacuum, thus preparing methanol extract of nutmeg (7 g). The extract was fractionated with ethylacetate, butanol and water. The ethylacetate fraction (4.2 g) was gained. It was eluted by silica gel column chromatography (Merck Kieselgel 66; 70-230 mesh) with a mixed solution of hexane and ethylacetate with a ratio of 10:1 (v/v) to obtain fraction III (1 g). The fraction III was subjected to column chromatography with a mixed solvent of hexane and ethylacetate with a ratio of 20:1 (v/v) to obtain fraction III-B (0.52 g). Then, the fraction III-B was eluted by preparative Rp-18 column chromatography (Merk LiChroprep:25-40 μm) with 80% methanol to obtain single material fraction III-B-2 (0.5 g). This separation process is shown in FIG. 6.

<39-2> Structural Analysis

To determine the structure of the separated single material III-B-2, the $^{13}$C-NMR spectrum and $^1$H-NMR spectrum of the material were measured at 600 MHz and 150 MHz (solvent: DMSO), respectively. To measure $^1$H-$^1$H correlation and $^1$H-$^{13}$C correlation on the basis of the results of the $^{13}$C-NMR spectrum and the $^1$H-NMR spectrum, the $^1$H-$^1$H COSY spectrum and the $^1$H-$^{13}$C HMBC spectrum were measured. The results of comprehensive analysis of 1H-NMR, $^{13}$C-NMR, $^1$H-$^1$H COSY and $^1$H-$^{13}$C-HMBC are shown in Table 17 blow.

TABLE 17

| Position | $^{13}$C-NMR | $^1$H-NMR | $^1$H-$^1$H COSY | $^1$H-$^{13}$C HMBC |
|---|---|---|---|---|
| 1 | 135.4 | | | |
| 2 | 109.2 | 6.72 brs | | C-7, C-6, C-4, C-3 |
| 3 | 147.3 | | | |
| 4 | 145.1 | | | |
| 5 | 107.9 | 6.79 d(7.8) | 6.61 | C-6, C-4, C-3, C-1 |
| 6 | 121.7 | 6.61 dd(7.8) | 6.79 | C-7, C-5, C-4, C-2, C-1 |
| 7 | 38.2 | 2.23 dd(13.2, 9.3) | 1.64, 2.66 1.64, 2.23 | C-8, C-6, C-2, C-1 |

TABLE 17-continued

| Position | $^{13}$C-NMR | $^{1}$H-NMR | $^{1}$H-$^{1}$H COSY | $^{1}$H-$^{13}$C HMBC |
|---|---|---|---|---|
| | | 2.66 dd(13.2, 4.8) | | C-9, C-8, C-6, C-2, C-1 |
| 8 | 38.7 | 1.64 brs | 0.75, 2.23, 2.66 | C-7 |
| 9 | 16.0 | 0.75 d(6.3) | 1.64 | C-8, C-7 |
| 1' | 132.4 | | | |
| 2' | 112.9 | 6.66 brs | | C-7', C-6', C-4', C-3' |
| 3' | 147.1 | | | |
| 4' | 144.4 | | | |
| 5' | 115.2 | 6.66 d(7.9) | 6.53 | C-6', C-4', C-3', C-1' |
| 6' | 121.0 | 6.53 d(7.9, 1.1) | 6.66 | C-7', C-5', C-4', C-2', C-1' |
| 7' | 38.0 | 2.17 dd(13.2, 9.3) | 1.64, 2.66 1.64, 2.17 | C-8', C-6', C-2', C-1' |
| | | 2.66 dd(13.2, 4.8) | | C-9', C-8', C-6', C-2', C-1' |
| 8' | 38.7 | 1.64 brs | 0.75, 2.17, 2.66 | C-7' |
| 9' | 16.1 | 0.75 d(6.3) | 1.64 | C-8', C-7' |
| OMe | 55.5 | 3.72 (s) | | |
| O—CH$_2$—O | 100.6 | 5.95 d(4.8) | | C-3, C-4 |

<39-3> Mass Analysis

In order to analyse the mass of the single material, III-B-2, EI/MS was measured, and the [M]$^+$ of the single material was observed at m/z 328 in EI/MS, suggesting that the material had a molecular weight of 328 and a molecular formula of $C_{20}H_{24}O_4$.

<39-4> Measurement of Specific Rotation 20 mg of the single material, III-B-2, was disolved with 2 ml of chloroform (CHCl$_3$) and measured specific rotation ([α]$_D$) by using Polarimeter (Automatic Polarimeter, APIII-589, Rodulph, N.J., USA), as a result, [α]=+4.0 (CHCl$_3$, c=1.0)

Through the above results of $^1$H-NMR, $^{13}$C-NMR, COSY and $^1$H-$^{13}$C-HMBC, EI/MS and [α]$_D$) and the prior reference (Woo, W. S. at al., *Phytochemistry*, 26: 1542-1543, 1987), the separated single material was found to be macelignan represented by the following formula 4:

<Formula 4>

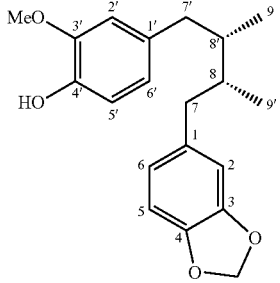

TEST EXAMPLE 9

Measurement of Expression Levels of Matrix Metalloproteinase-1 (MMP-1) in Cells when Treated with Macelignan In order to measure the matrix metalloproteinase-1 (MMP-1) inhibitory activity effect of macelignan, they were compared that the testing group which was treated with macelignan in different concentration of 3, 5 and 10 μM by using western blot method of Example 3, and as a result, they showed matrix metalloproteinase-1 (MMP-1) inhibitory activity effect of 31%, 42%, and 63%, respectively compared with UV 20 J/cm$^2$ treated positive control group.

This means macelignan of the present invention showed the effect on inhibiting expression of matrix metalloproteinase-1 which is marker of antiaging.

EXAMPLE 40

Measurement of Expression Levels of Matrix Metalloproteinase-1 (MMP-1) in Cells when Treated with Ethanol Extract of the Nutmeg 100 g of the dried and ground nutmeg was added to 400 ml of ethanol and left to stand at room temperature for 2 days. The extracted solution was filtered and concentrated in a vacuum, thus preparing a ethanol extract of nutmeg (12.7 g).

Concerning the above extract, measurement of expression levels of matrix metalloproteinase-1 (MMP-1) was performed as shown in Example 3 and then as a result, the expression levels of matrix metalloproteinase-1 (MMP-1) of the group which was treated with 5 μg/ml and 10 μg/ml of ethanol extract decreased 38% and 75% respectively than positive control group which was treated with 20 J/cm$^2$ of UV.

EXAMPLE 41

Measurement of Expression Levels of Matrix Metalloproteinase-1 (MMP-1) in Cells when Treated with, Hexane Extract of the Nutmeg 100 g of the dried and ground nutmeg was added to 400 ml of hexane and left to stand at room temperature for 2 days. The extracted solution was filtered and concentrated in a vacuum, thus preparing a hexane extract of nutmeg (26.6 g). Concerning the above extract, measurement of expression levels of matrix metalloproteinase-1 (MMP-1) was performed as shown in Example 3 and then as a result, the expression levels of matrix metalloproteinase-1 (MMP-1) of the group which was treated with 5 μg/ml and 10 μg/ml of hexane extract decreased 32% and 68% respectively than positive control group which was treated with 20 J/cm$^2$ of UV.

TEST EXAMPLE 10

In Vivo Confirmation of Anti-Wrinkle Effect of the Axtract of the Nutmeg and Macelignan 6-week hairless mouse (Skh; HR-1) have a quarantine period for 1 week before experiment, and cared maintaining temperature with 23±3° C., relative humidity with 50±5° C., and 12 hours of day/night cycle (07:00-19:00/day time). They were fed with feed for mouse, and tap water. UV irradiations were performed 3 times per week in the same time, the amount of the UV irradiations were 50 mJ/cm$^2$ on 1$^{st}$ week, 100 mJ/cm$^2$ on 2$^{nd}$ week, 200 mJ/cm$^2$ on 3$^{rd}$ week, and 250 mJ/cm$^2$ on 4$^{th}$ and after 4$^{th}$ weeks. The groups were divided into 4 groups. Those were control, UV control, UV/nutmeg and UV/macelignan.

50 μl of 6% (w/v) of nutmeg extract and 20 mM macelignan solution were applied for the experiment. For the experiment, nutmeg extract and macelignan were disolved in ethanol: polyethylene glycol (7:3, v/v).

Figure 7:
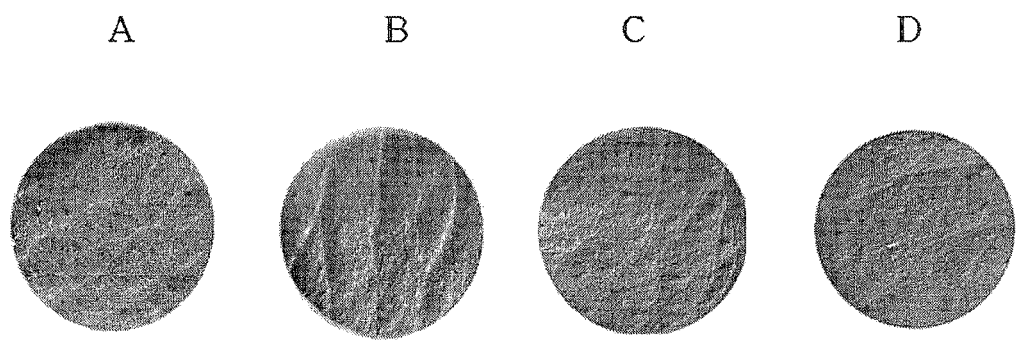
FIG. 7 is a photo confirming wrinkle reducing effect of the extract of the present invention and lignan compounds when they were applied to the skin.

After experiment, to determine the effect on reducing wrinkle, replica of hairless mice back was sampled by using siliconpolymer (SILFLO impression material), as a result, as shown in FIG. 7, it were confirmed that both groups which were applied nutmeg extract and macelignan after UV irradiation inhibited wrinkle compared with the UV positive group. In FIG. 7, A is the normal group, B is the UV irradiated group, C is the nutmeg applying group, and D is the macelignan applying group.

TEST EXAMPLE 11

In Vivo Confirmation of Anti-Wrinkle Effect of the Axtract of the Nutmeg and Macelignan by Oral Administration 6-week hairless mouse (Skh; HR-1) have a quarantine period for 1 week before experiment, and cared maintaining temperature with 23±3° C., relative humidity with 50±5° C., and 12 hours of day/night cycle (07:00-19:00/day time). They were fed with feed for mouse, and tap water. UV irradiations were performed 3 times per week in the same time, the amount of the UV irradiations were 50 mJ/cm$^2$ on 1$^{st}$ week, 100 mJ/cm$^2$ on 2$^{nd}$ week, 200 mJ/cm$^2$ on 3$^{rd}$ week, and 250 mJ/cm$^2$ on 4$^{th}$ and after 4$^{th}$ weeks. The groups were divided into 4 groups. Those were control, UV control, UV/nutmeg and UV/macelignan. 200 mg/kg of nutmeg and 20 mg/kg of macelignan were administered respectively by oral. For the experiment, nutmeg extract and macelignan were disolved in 0.25% CMC (carboxyl methyl celluose) solution.

Figure 8:
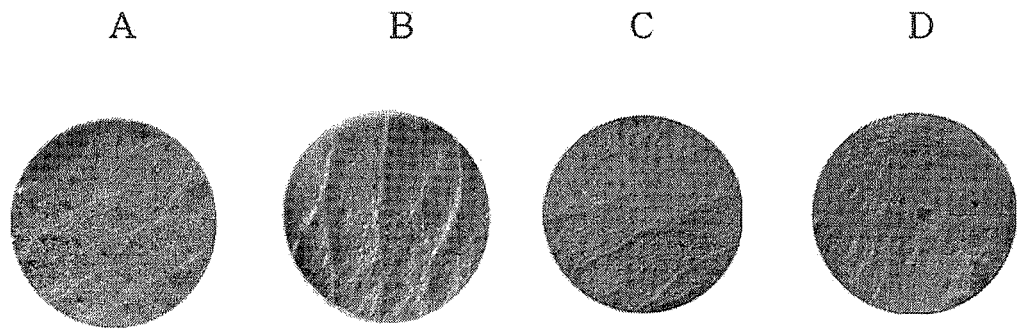
FIG. 8 is a photo confirming wrinkle reducing effect of the extract of the present invention and lignan compounds when they were orally administered.

After experiment, to determine the effect on inhibiting wrinkle, replica of hairless mice back was sampled by using siliconpolymer (SILFLO impression material), as a result, as shown in FIG. 8, it were confirmed that both groups which were administered nutmeg extract and macelignan by oral after UV irradiation inhibited wrinkle compared with the UV positive group. In FIG. 8, A is the normal group, B is the UV irradiated group, C is the nutmeg administering group, and D is the macelignan administering group.

EXAMPLEs 42 to 45

Preparation of Lotions Containing Macelignan macelignan of the present invention was used to prepare lotions having compositions of Examples 42 to 45. Macelignan was dissolved in water at 4 concentrations of 5.0 wt %, 0.1 wt %, 0.01 wt %, and 0.001 wt % and mixed with phosphoric acid solution. The solution was mixed with ethanol, glycerin, propyleneglycol and added fragrance and preservative, and then, the weight thereof was adjusted with water. Then, the solution was uniformly stirred (Table 18).

TABLE 18

| component | Example 42 | Example 43 | Example 44 | Example 45 |
|---|---|---|---|---|
| 1. macelignan (%) | 5.0 | 0.1 | 0.01 | 0.001 |
| 2. glycerin(%) | 2.0 | 2.0 | 2.0 | 2.0 |
| 3. prolyleneglycol(%) | 2.0 | 2.0 | 2.0 | 2.0 |
| 4. potassium phosphate (%) | 0.1 | 0.1 | 0.1 | 0.1 |
| 5. sodium phosphate dibasic (%) | 0.05 | 0.05 | 0.05 | 0.05 |
| 6. fragrance (%) | 0.02 | 0.02 | 0.02 | 0.02 |
| 7. ethanol(96%)(%) | 20 | 20 | 20 | 20 |
| 8. Purified water(%) | balance | balance | balance | balance |
| 9. Preservative (%) | qs | qs | qs | qs |

EXAMPLEs 46 to 49

Preparation of Creams Containing an Macelignan

Macelignan of the present invention was used to prepare creams having compositions of Examples 46 to 49. First, materials (2)-(6) were dissolved at 75-80° C., and materials (7)-(10) were dissolved at the same temperature. The materials (7)-(10) were emulsified in the materials (2)-(6), and then macelignan was added thereto at each of concentrations of 5.0 wt %, 0.1 wt % 0.01% and 0.001% and the emulsions were stirred. Finally, fragrance was added thereto and the balance of purified water was added (Table 19).

TABLE 19

| component | Example 46 | Example 47 | Example 48 | Example 49 |
|---|---|---|---|---|
| 1. macelignan (%) | 5.0 | 0.1 | 0.01 | 0.001 |
| 2. glycerin | 2.0 | 2.0 | 2.0 | 2.0 |
| 3. propyleneglycol | 2.0 | 2.0 | 2.0 | 2.0 |
| 4. chlorolauryl sulfide | 8.0 | 8.0 | 8.0 | 8.0 |
| 5. stearin | 5.4 | 5.4 | 5.4 | 5.4 |
| 6. mineral oil | 4.5 | 4.5 | 4.5 | 4.5 |
| 7. fragrance | 0.02 | 0.02 | 0.02 | 0.02 |
| 8. cetyl alcohol | 6.5 | 6.5 | 6.5 | 6.5 |
| 9. purified water | balance | balance | balance | balance |
| 10. preservative | qs | qs | qs | qs |

TEST EXAMPLE 11

In Vivo Measurement of Collagen Synthesis of Macelignan-Containing Composition

Hairless mice were radiated with UV light at a dose of 20 J/cm$^2$ one time everyday for 4 weeks, and then 100 ml of each of macelignan-containing compositions of Examples 40 to 47 was applied to the back of the mice. Then, the mice were biopsied, and the formation of collagen in the biopsied tissue was histologically measured. Herein, the measurement of the amount of newly produced collagen was carried out by immunostaining the tissue and subjecting the immunostained tissue to image analysis. The measurement results are shown in Table 20 below.

TABLE 20

| Result | Increase (%) in collagen |
|---|---|
| Control | 0 |
| Lotion Example 42 | 66.9 |
| Lotion Example 43 | 29.2 |
| Lotion Example 44 | 16.4 |
| Lotion Example 45 | 7.5 |
| Control | 0 |
| Cream Example 46 | 69.8 |
| Cream Example 47 | 35.9 |
| Cream Example 48 | 17.8 |
| Cream Example 49 | 8.1 |

As can be seen in Table 20, the increase in macelignan led to the increase in collagen synthesis, and the activity of the extract was higher in the creams than in the lotions. This is believed to be because the retention of the creams in the skin is higher than that of the lotions.

EXAMPLEs 50 to 53

Preparation of Beverages Containing Macelignan of the Present Invention

According to the conventional preparation method, the components of the table 21 (total volume: 1000 ml) were mixed and stirred at 85° C. for 1 hr, and then prepared a beverage containing macelignan of the present invention by sterilizing the above solution.

TABLE 21

| component | Example 50 | Example 51 | Example 52 | Example 53 |
|---|---|---|---|---|
| Lignan compound of the present invention | Fragrin A 1000 mg | austobailignan 7 1000 mg | licarin E 1000 mg | macelignan 1000 mg |
| Citric acid | 1000 mg | 1000 mg | 1000 mg | 1000 mg |
| Oligosaccharide | 100 g | 100 g | 100 g | 100 g |
| taurin | 1000 mg | 1000 mg | 1000 mg | 1000 mg |
| purified water | balance | balance | balance | balance |

Industrial Applicability

As can be seen from the foregoing, an extract of nutmeg or an extract of the aril of nutmeg and fragrin A, austobailignan 7, licarin E, and macelignan which are extracted from thereof of the present invention have activities in suppressing collagen degradation enzyme-1 (MMP-1, matrix metalloproteinase-1) and formation of new collagen (type-1 procollagen), thereby have effect on anti-wrinkle. Accordingly, an extract of nutmeg or an extract of the aril of nutmeg and fragrin A, austobailignan 7, licarin E, and macelignan which are extracted from thereof of the present invention may be useful for preventing or treating wrinkle caused by photoaging.

The invention claimed is:

1. A method for reducing skin wrinkles comprising administering or applying an effective amount of an isolated lignan compound selected from the group consisting of fragrin A represented by Formula 1, austobailignan 7 represented by Formula 2, licarin E represented by Formula 3, and macelignan represented by Formula 4 to a subject in need thereof.

2. A method for inducing collagen synthesis in skin comprising administering or applying an effective amount of an isolated lignan compound selected from the group consisting of fragrin A represented by Formula 1, austobailignan 7represented by Formula 2, licarin E represented by Formula 3, and macelignan represented by Formula 4 to a subject in need thereof.

3. A method for suppressing collagen decomposition in skin comprising administering or applying an effective amount of an isolated lignan compound which is selected from the group consisting of fragrin A represented by Formula I, austobailignan 7 represented by Formula 2, licarin E represented by Formula 3, and macelignan represented by Formula 4 to a subject in need thereof.

* * * * *